US010255694B2

(12) United States Patent
Feng et al.

(10) Patent No.: US 10,255,694 B2
(45) Date of Patent: Apr. 9, 2019

(54) METHODS AND SYSTEMS FOR EMISSION COMPUTED TOMOGRAPHY IMAGE RECONSTRUCTION

(71) Applicant: UIH AMERICA, INC., Houston, TX (US)

(72) Inventors: Tao Feng, Houston, TX (US); Wentao Zhu, Houston, TX (US); Hongdi Li, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 0 days.

(21) Appl. No.: 15/386,048

(22) Filed: Dec. 21, 2016

(65) Prior Publication Data

US 2018/0174333 A1    Jun. 21, 2018

(51) Int. Cl.
| | |
|---|---|
| *G06T 11/00* | (2006.01) |
| *G06T 7/207* | (2017.01) |
| *A61B 6/00* | (2006.01) |
| *A61B 5/00* | (2006.01) |
| *A61B 6/03* | (2006.01) |

(52) U.S. Cl.
CPC .......... *G06T 11/003* (2013.01); *A61B 5/7289* (2013.01); *A61B 5/7292* (2013.01); *A61B 6/037* (2013.01); *A61B 6/5205* (2013.01); *A61B 6/5264* (2013.01); *G06T 7/207* (2017.01)

(58) Field of Classification Search
CPC ..... A61B 6/037; A61B 6/5264; A61B 5/0044; A61B 5/7207; A61B 5/7289; A61B 5/7292; G06T 7/0012; G06T 5/002; G06T 11/003; G06T 7/20; G06T 2207/10081; G06T 2207/30048; G06T 11/005; G06T 2207/10108; G06T 7/207
See application file for complete search history.

(56) References Cited

U.S. PATENT DOCUMENTS

| | | | |
|---|---|---|---|
| 7,545,903 B2 * | 6/2009 | Kohler | ........................ G06T 7/20 378/4 |
| 7,782,998 B2 * | 8/2010 | Langan | ................. G01N 23/046 378/8 |
| 8,098,916 B2 * | 1/2012 | Thielemans | ........... A61B 6/032 382/131 |
| 8,107,695 B2 * | 1/2012 | Wollenweber | ............ G06T 7/20 382/107 |

(Continued)

OTHER PUBLICATIONS

International Search report in International Application No. PCT/US17/40185 dated Sep. 22, 2017, 2 pages.

(Continued)

*Primary Examiner* — Manav Seth
(74) *Attorney, Agent, or Firm* — Metis IP LLC

(57) ABSTRACT

The present disclosure relates to systems and methods for reconstructing an Emission Computed Tomography (ECT) image. The systems, having at least one machine each of which has at least one processor and storage, may perform the methods to obtain ECT projection data, the ECT projection data corresponding to a plurality of voxels; determine a plurality of gate numbers for the plurality of voxels, the plurality of gate numbers relating to motion information of the plurality of voxels; and reconstruct an ECT image based on the ECT projection data and the plurality of gate numbers.

19 Claims, 8 Drawing Sheets

(56) References Cited

U.S. PATENT DOCUMENTS

| | | | | |
|---|---|---|---|---|
| 8,131,044 B2* | 3/2012 | Wollenweber | | A61B 6/032 |
| | | | | 382/131 |
| 8,437,524 B2* | 5/2013 | Bontus | | A61B 6/032 |
| | | | | 382/131 |
| 8,483,432 B2* | 7/2013 | Patwardhan | | G06T 7/0012 |
| | | | | 382/103 |
| 8,600,132 B2* | 12/2013 | Razifar | | A61B 6/032 |
| | | | | 382/128 |
| 8,611,630 B1* | 12/2013 | Katsevich | | G06T 7/0012 |
| | | | | 382/131 |
| 8,879,814 B2* | 11/2014 | Wollenweber | | A61B 6/032 |
| | | | | 382/131 |
| 8,965,094 B2* | 2/2015 | Peacock, III | | G01R 33/4625 |
| | | | | 128/922 |
| 9,031,300 B1* | 5/2015 | Manjeshwar | | G06T 11/003 |
| | | | | 382/128 |
| 9,305,377 B2 | 4/2016 | Olivier et al. | | |
| 2008/0219527 A1 | 9/2008 | Lavi et al. | | |
| 2010/0290683 A1* | 11/2010 | Demeester | | A61B 6/037 |
| | | | | 382/131 |
| 2012/0305780 A1 | 12/2012 | Thiruvenkadam et al. | | |
| 2013/0197347 A1* | 8/2013 | Moghari | | A61B 5/7207 |
| | | | | 600/410 |
| 2013/0315459 A1* | 11/2013 | Wollenweber | | A61B 6/032 |
| | | | | 382/131 |
| 2014/0133717 A1* | 5/2014 | Kabus | | A61B 6/5264 |
| | | | | 382/128 |
| 2014/0270450 A1* | 9/2014 | Grass | | A61B 6/032 |
| | | | | 382/131 |
| 2015/0036905 A1* | 2/2015 | Mueller | | G06T 15/08 |
| | | | | 382/131 |
| 2015/0339821 A1 | 11/2015 | Gopalakrishnan et al. | | |
| 2016/0324500 A1 | 11/2016 | Fan et al. | | |
| 2017/0052119 A1 | 2/2017 | Kumar et al. | | |

OTHER PUBLICATIONS

Written opinion in International Application No. PCT/US17/40185 dated Sep. 22, 2017, 6 pages.

Johan Nuyis et al., ML-reconstruction for TOF-PET with Simultaneous Estimation of the Attenuation Factors, Nuclear Science Symposium & Medical Imaging Conference, 2012.

* cited by examiner

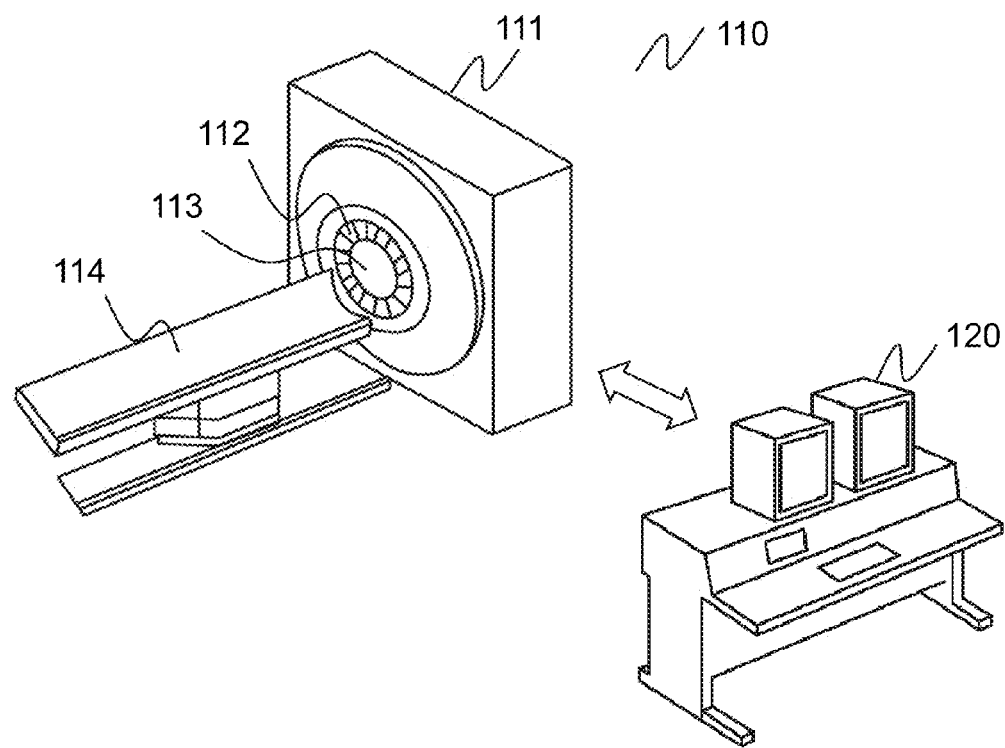
FIG. 1-A
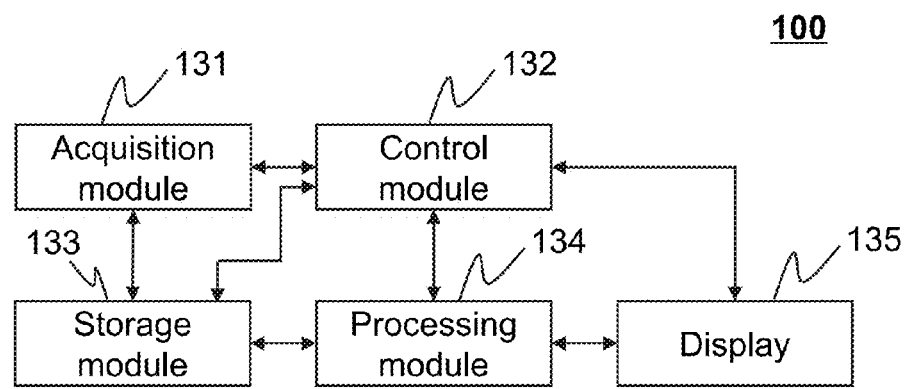
FIG. 1-B

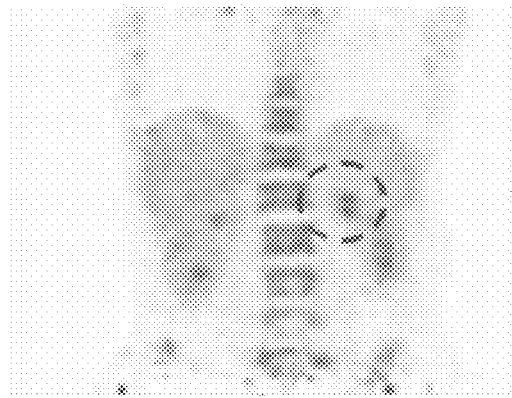
FIG. 7-A
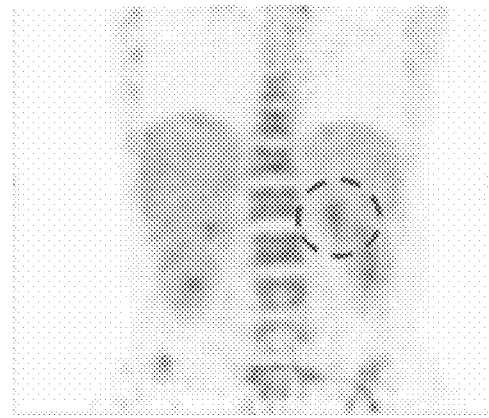 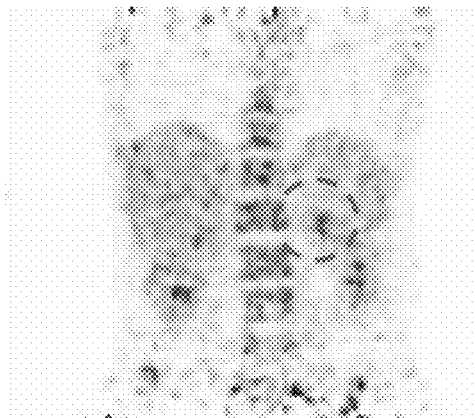
FIG. 7-B  FIG. 7-C

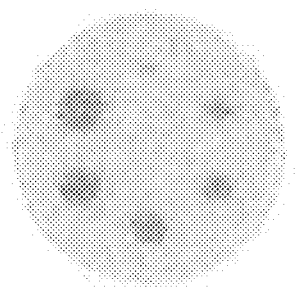
FIG. 8-A
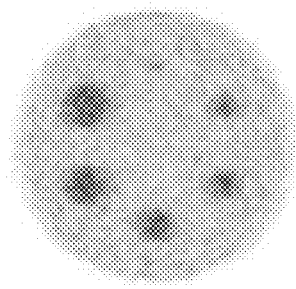
FIG. 8-B
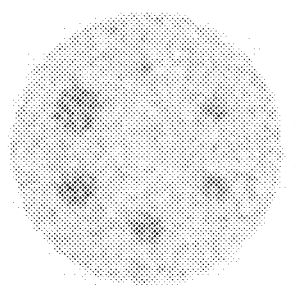
FIG. 8-C

METHODS AND SYSTEMS FOR EMISSION COMPUTED TOMOGRAPHY IMAGE RECONSTRUCTION

TECHNICAL FIELD

The present disclosure generally relates to image reconstruction, and more specifically relates to methods and systems for reconstructing an Emission Computed Tomography (ECT) image.

BACKGROUND

Emission Computed Tomography (ECT) has been widely used in medicine for diagnosis and other purposes. Types of ECT include Positron Emission Tomography (PET) and Single-Photon Emission Computed Tomography (SPECT). A subject, such as a patient, may be scanned by an ECT scanner to obtain ECT images. When ECT is used for chest or upper abdomen examinations, respiratory motion of the lungs and/or cardiac movements of the heart of a subject may lead to motion blur in the ECT images. It is desirable to provide systems and methods for reconstructing an ECT image with improved quality and reduced motion blur.

SUMMARY

In a first aspect of the present disclosure, a method implemented on at least one machine each of which has at least one processor and storage for reconstructing an Emission Computed Tomography (ECT) image is provided. The method may include one or more of the following operations. ECT projection data may be obtained. The ECT projection data may correspond to a plurality of voxels in reconstructed image domain. A plurality of gate numbers for the plurality of voxels may be determined. The plurality of gate numbers may relate to motion information of the plurality of voxels. An ECT image may be reconstructed based on the ECT projection data and the plurality of gate numbers.

In some embodiments, the ECT projection data may include four-dimensional (4D) Single Photon emission Computed Tomography (SPECT) data, 4D Positron Emission Tomography (PET) data, or 4D Computed Tomography (CT) data.

In some embodiments, each of the gate numbers may correspond to one or more of the plurality of voxels.

In some embodiments, a plurality of motion ranges of the plurality of voxels may be obtained from a population-based distribution. The plurality of gate numbers may be determined based on the plurality of motion ranges.

In some embodiments, an intermediate image may be generated based on the ECT projection data. A difference between the plurality of voxels at a first time point and the plurality of voxels at a second time point may be determined based on the intermediate image. A difference image may be determined based on the difference. The plurality of gate numbers may be determined based on the difference image.

In some embodiments, a feature relating to the motion information of the plurality of voxels may be determined based on the plurality of gate numbers. The ECT image may be reconstructed based on the feature.

In some embodiments, a temporal spread function may be determined based on the plurality of gate numbers. The feature relating to the motion information of the plurality of voxels may be obtained based on the temporal spread function.

In some embodiments, the temporal spread function may be a blurring function.

In some embodiments, the feature may include a Full Width at Half Maximum of the temporal spread function.

In some embodiments, a threshold relating to the plurality of gate numbers may be determined. The Full Width at Half Maximum of the temporal spread function may be determined based on the plurality of gate numbers and the threshold.

In some embodiments, the threshold relating to the plurality of gate numbers may be the maximum one of the plurality of gate numbers.

In some embodiments, a first gate number may be determined for a first voxel of the plurality of voxels. A second gate number may be determined for a second voxel of the plurality of voxels. The second gate number may differ from the first gate number.

In some embodiments, a first Full Width at Half Maximum of a first temporal spread function may be determined for the first voxel. The first Full Width at Half Maximum may correspond to a first motion range of the first voxel. A second Full Width at Half Maximum of a second temporal spread function may be determined for the second voxel. The second Full Width at Half Maximum may correspond to a second motion range of the second voxel. The second Full Width at Half Maximum may differ from the first Full Width at Half Maximum.

In a second aspect of the present disclosure, a method for reconstructing an Emission Computed Tomography (ECT) image is provided. The method may include one or more of the following operations. ECT projection data of a subject may be obtained. An intermediate image may be generated based on the ECT projection data, wherein the intermediate image may include a plurality of voxels. A plurality of gate numbers may be determined for the plurality of voxels in the intermediate image. The plurality of gate numbers may relate to motion information of the plurality of voxels. An ECT image of the subject may be reconstructed based on the ECT projection data and the plurality of gate numbers.

In some embodiments, a difference between the plurality of voxels at a first time point and the plurality of voxels at a second time point in the intermediate image may be determined. A difference image may be determined using the difference. The plurality of gate numbers may be determined based on the difference image.

In some embodiments, the ECT projection data of the subject may be sorted into a plurality of bins according to the plurality of gate numbers. The ECT image may be reconstruct based on at least one of the plurality of bins.

In some embodiments, the ECT projection data may include at least one of 4D SPECT data, 4D PET data, or 4D CT data.

In some embodiments, a temporal spread function may be determined based on the plurality of gate numbers. At least a feature may be determined based on the temporal spread function, wherein the feature relates to the motion information of the plurality of voxels. The ECT image of the subject may be reconstructed based on the ECT projection data and the feature relating to the motion information of the plurality of voxels.

In a third aspect of the present disclosure, an Emission Computed Tomography (ECT) system is provided. The system may include a set of instructions for ECT image reconstruction and one or more processors. When the one or more processors executing the set of instructions, the one or more processors are directed to perform one more of the following operations. The one or more processors may obtain ECT projection data. The ECT projection data may correspond to a plurality of voxels. The one or more processors may determine a plurality of gate numbers for the plurality of voxels. The plurality of gate numbers may relate to motion information of the plurality of voxels. The one or more processors may reconstruct an ECT image based on the ECT projection data and the plurality of gate numbers.

In a fourth aspect of the present disclosure, a device including a non-transitory computer readable medium is provided. The non-transitory computer readable medium may include executable instructions that when executed by at least one processor, cause the at least one processor to effectuate a method including one or more of the following operations. ECT projection data may be obtained. The ECT projection data may correspond to a plurality of voxels in reconstructed image domain. A plurality of gate numbers for the plurality of voxels may be determined. The plurality of gate numbers may relate to motion information of the plurality of voxels. An ECT image may be reconstructed based on the ECT projection data and the plurality of gate numbers.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A is a schematic diagram illustrating an exemplary ECT system according to some embodiments of the present disclosure;

FIG. 1-B is a block diagram illustrating an exemplary image processing system according to some embodiments of the present disclosure;

FIG. 7-A through FIG. 7-C illustrate exemplary ECT images generated by different image reconstruction methods according to some embodiments of the present disclosure; and FIG. 8-A through FIG. 8-C illustrate exemplary ECT images generated by different image reconstruction methods according to some embodiments of the present disclosure.

DETAILED DESCRIPTION

Figure 2:
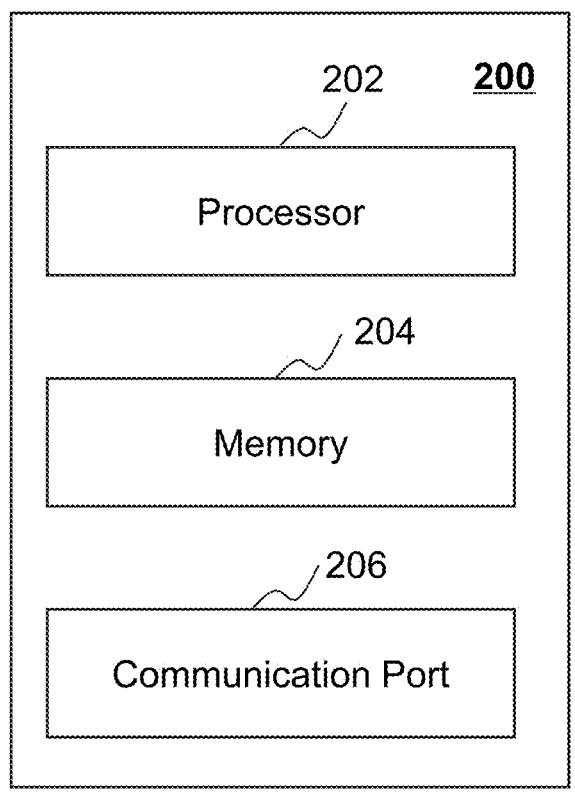
FIG. 2 is a block diagram illustrating exemplary hardware and/or software components of an exemplary computing device according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be an emission computed tomography (ECT) system, a computed tomography (CT) system, a magnetic resonance imaging(MRI) system, an ultrasonography system, a multi-modality system, or the like, or any combination thereof. The ECT system may include a positron emission tomography (PET) system, a single photon emission computed tomography (SPECT) system, etc. Exemplary multi-modality system may include a computed tomography-positron emission tomography (CT-PET) system, a magnetic resonance-positron emission tomography (MR-PET) system, etc. In some embodiments, the multi-modality imaging system may include modules and/or components for performing ECT imaging and/or related analysis.

For illustration purposes, the disclosure describes systems and methods for ECT image reconstruction. The imaging system may reconstruct an ECT image based on a gating approach. As used herein, a gating approach may refer to that ECT data may be divided into a plurality of sections and one of the sections may be selected to be processed to generate an ECT image. For example, the imaging system may sort the ECT data acquired from a subject into a plurality of bins based on one or more gate numbers and reconstruct an ECT image based on at least one of the plurality of bins. As another example, the imaging system may reconstruct an ECT image by applying different gate numbers to the ECT data corresponding to different spatial points of a subject.

The following description is provided to help better understanding ECT image reconstruction methods or systems. The term "image" used in this disclosure may refer to a 2D image, a 3D image, a 4D image, or any related image data (e.g., the ECT data, projection data corresponding to the ECT data). The image data may correspond to a distribution of an ECT tracer molecules within the subject. As used herein, the ECT tracer may refer to a substance that may undergo certain changes under the influence of an activity and/or functionality within the subject, whose activity and/or functionality may be visualized and/or studied. This is not intended to limit the scope the present disclosure. For persons having ordinary skills in the art, a certain amount of variations, changes, and/or modifications may be deducted under guidance of the present disclosure. Those variations, changes, and/or modifications do not depart from the scope of the present disclosure.

FIG. 1-A is a schematic diagram illustrating an exemplary ECT system according to some embodiments of the present disclosure. The ECT system may include an ECT scanner 110 and a host computer 120. ECT scanner 110 may include a gantry 111, a detector 112, a detecting region 113, and a subject table 114.

Detector 112 may detect radiation events (e.g., gamma photons) emitted from detecting region 113. In some embodiments, detector 112 may include a plurality of detector units. The detector units may be implemented in any suitable manner, for example, a ring, a rectangle, or an array. In some embodiments, the detector unit may include one or more crystal elements and/or one or more photomultiplier tubes (PMT) (not shown). In some embodiments, a PMT as employed in the present disclosure may be a single-channel PMT or a multi-channel PMT. Subject table 114 may position a subject in detecting region 113.

In some embodiments, the detected radiation events may be stored or archived in a storage (e.g., a storage device in host computer 120), displayed on a display (e.g., a screen on host computer 120), or transferred to any relating device (e.g., an external database). In some embodiments, a user may control ECT scanner 110 via host computer 120.

Further, while not shown, the ECT system may be connected to a network (e.g., a telecommunications network, a local area network (LAN), a wireless network, a wide area network (WAN) such as the Internet, a peer-to-peer network, a cable network, etc.) for communication purposes.

It should be noted that the above description of the ECT system is merely provided for the purposes of illustration, and not intended to limit the scope of the present disclosure. For persons having ordinary skills in the art, multiple variations and modifications may be made under the teachings of the present disclosure. For example, the assembly and/or function of the ECT system may be varied or changed according to specific implementation scenarios. Merely by way of example, some other components may be added into the ECT system, such as a patient positioning module, a gradient amplifier module, and other devices or modules.

FIG. 1-B is a block diagram illustrating an exemplary image processing system 100 according to some embodiments of the present disclosure. Image processing system 100 may be implemented via host computer 120. As illustrated in FIG. 1-B, image processing system 100 may include an acquisition module 131, a control module 132, a storage module 133, a processing module 134, and a display 135.

Acquisition module 131 may acquire or receive ECT data. The ECT data may include SPECT data, PCT data, or CT data. The ECT data may be a data set. In some embodiments, the ECT data may be list-mode data or sinogram data. Merely by way of example with reference to a PET system, acquisition module 131 may acquire or receive PET data. In some embodiments, during a PET scan or analysis, PET tracer (also referred to as "PET tracer molecules") are first introduced into the subject before an imaging process begins. During the PET scan, the PET tracer molecules may emit positrons, namely the antiparticles of electrons. A positron has the same mass and the opposite electrical charge as an electron, and it undergoes an annihilation (also referred to as an "annihilation event" or a "coincidence event") with an electron (that may naturally exist in abundance within the subject) as the two particles collide. An electron-positron annihilation may result in two 511 keV gamma photons, which, upon their own generation, begin to travel in opposite directions with respect to one another. The line connecting the two gamma photons may be referred to as a "line of response (LOR)." Acquisition module 131 may obtain the trajectory and/or information of the gamma photons (also referred to as the "PET data"). For example, the PET data may include a list of annihilation events, transverse and longitudinal positions of the LORs, or the like, or a combination thereof. In some embodiments, the PET data may be used to determine the locations and/or the concentration distribution of the PET tracer molecules within the subject.

In some embodiments, the PET tracer may include carbon (11C), nitrogen (13N), oxygen (15O), fluorine (18F), or the like, or a combination thereof. In some embodiments, for a SPECT system, a SPECT tracer may be introduced into the subject. The SPECT tracer may include technetium-99m, iodine-123, indium-111, iodine-131, or the like, or a combination thereof. Accordingly, in some embodiments, the PET tracer or SPECT tracer of the present disclosure may be organic compounds containing one or more of such isotopes. These tracers are either similar to naturally occurring substances or otherwise capable of interacting with the functionality or activity of interest within the subject. Hence, distributional information of the tracer may be reliably used as an indicator of the subject functionality. In some embodiments, the PET tracer and the SPECT tracer may be collectively referred to as "ECT tracer."

Control module 132 may generate a control parameter for acquisition module 131, storage module 133, processing module 134, and display 135. For example, control module 132 may control acquisition module 131 as to whether to acquire a signal, or the time when a signal acquisition may occur. As another example, control module 132 may control processing module 134 to select different algorithms to process the ECT data acquired by acquisition module 131. In some embodiments, control module 132 may receive a real-time or a predetermined command provided by a user (e.g., a doctor) and adjust acquisition module 131, and/or processing module 134 to take images of a subject according to the received command. In some embodiments, control module 132 may communicate with the other modules in image processing system 100 for exchanging information or data.

Storage module 133 may store the acquired ECT data, the control parameters, the processed ECT data, or the like, or a combination thereof. In some embodiments, storage 133 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, storage 133 may store one or more programs and/or instructions that may be executed by the processor(s) of image processing system 100 to perform exemplary methods described in this disclosure. For example, storage 133 may store program(s) and/or instruction(s) executed by the processor(s) of image processing system 100 to acquire ECT data, reconstruct an image based on the ECT data, or display any intermediate result or a resultant image.

Processing module 134 may process different kinds of information received from different modules in image processing system 100. In some embodiments, processing module 134 may process the ECT data acquired by acquisition module 131, or retrieved from storage module 133. In some embodiments, processing module 134 may reconstruct ECT images based on the ECT data, generate reports including one or more ECT images and/or other related information, or the like. For example, processing module 134 may process the ECT data based on a gating approach and reconstruct an ECT image based on the gated ECT data. As another example, processing module 134 may determine a plurality of gate numbers for the ECT data corresponding to a plurality of spatial points of the subject (e.g., chest, back, or the like).

Display 135 may display any information relating to image processing system 100. The information may include programs, software, algorithms, data, text, number, images, voice, or the like, or any combination thereof. In some embodiments, display 135 may include a liquid crystal display (LCD), a light emitting diode (LED) based display, a flat panel display, a cathode ray tube (CRT), a touch screen, or the like, or a combination thereof. The touch screen may include, for example, a resistance touch screen, a capacity touch screen, a plasma touch screen, a vector pressure sensing touch screen, an infrared touch screen, or the like, or a combination thereof.

In some embodiments, one or more modules illustrated in FIG. 1-B may be implemented in at least part of the exemplary ECT system illustrated in FIG. 1-A. For example, acquisition module 131, control module 132, storage module 133, processing module 134, and/or display 135 may be integrated into a console (not shown). Via the console, a user may set parameters for scanning, control the imaging procedure, control a parameter of the reconstruction of an image, view the reconstructed images, etc. In some embodiments, the console may be implemented via host computer 120.

FIG. 2 is a block diagram illustrating exemplary hardware and software components of computing device 200 on which image processing system 100 may be implemented according to some embodiments of the present disclosure. In some embodiments, computing device 200 may include a processor 202, a memory 204, and a communication port 206.

Processor 202 may execute computer instructions (program code) and perform functions of processing module 134 in accordance with techniques described herein. Computer instructions may include routines, programs, objects, components, data structures, procedures, modules, and functions, which perform particular functions described herein. For example, processor 202 may process the data or information received from acquisition module 131, control module 132, storage module 133, processing module 134, or any other component of image processing system 100. In some embodiments, processor 202 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof. For example, processor 202 may include a microcontroller to process the ECT data from ECT scanner 110 for image reconstruction.

Memory 204 may store the data or information received from acquisition module 131, control module 132, storage module 133, processing module 134, or any other component of image processing system 100. In some embodiments, memory 204 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, memory 204 may store one or more programs and/or instructions to perform exemplary methods described in the present disclosure. For example, memory 204 may store a program for processing module 134 for reconstructing an ECT image based on the ECT data.

Communication port 206 may transmit to and receive information or data from acquisition module 131, control module 132, storage module 133, processing module 134 via network. In some embodiments, communication port 206 may include a wired port (e.g., a Universal Serial Bus (USB) port, a High Definition Multimedia Interface (HDMI) port, or the like) or a wireless port (a Bluetooth port, an infrared interface, a WiFi port, or the like).

Figure 3:
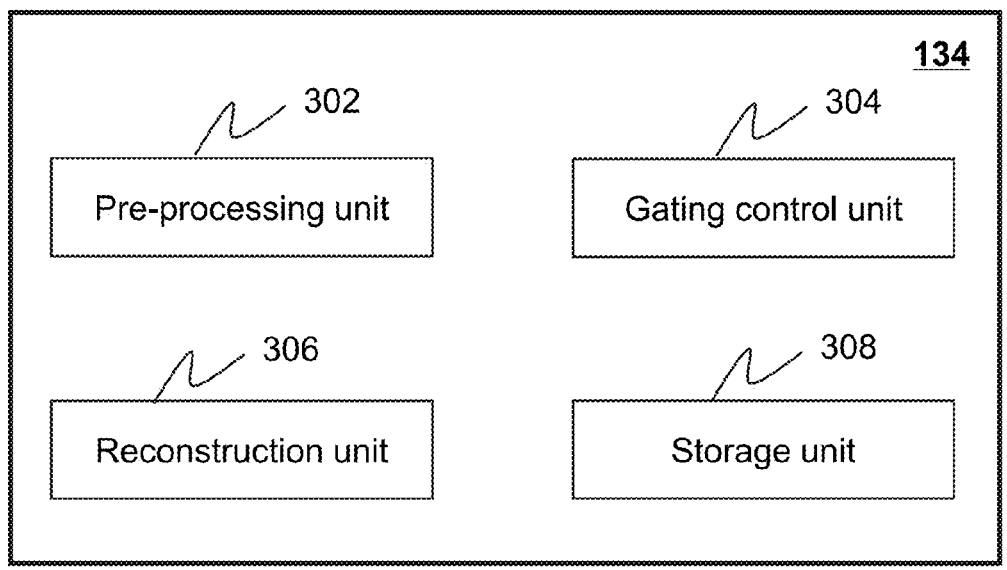
FIG. 3 is a block diagram illustrating an exemplary processing module according to some embodiments of the present disclosure.

FIG. 3 is a block diagram illustrating an exemplary processing module 134 according to some embodiments of the present disclosure. Processing module 134 may include a pre-processing unit 302, a gating control unit 304, a reconstruction unit 306, and a storage unit 308. In some embodiments, at least two of the units may be connected with each other via a wired connection (e.g., a metal cable, an optical cable, a hybrid cable, or the like, or any combination thereof) or a wireless connection (e.g., a Local Area Network (LAN), a Wide Area Network (WAN), a Bluetooth, a ZigBee, a Near Field Communication (NFC), or the like, or any combination thereof).

Pre-processing unit 302 may process different kinds of information received from acquisition module 131, control module 132, storage module 133, and/or display 135. The information may include the ECT data, basic information regarding a subject, a control parameter (e.g., acquisition frequency, acquisition rate, or the like), a display parameter (e.g., brightness, resolution, scale, or the like), or the like, or a combination thereof. Merely by way of example, pre-processing unit 302 may process the ECT data, for example, to remove or reduce noises.

Gating control unit 304 may determine a gating parameter (e.g., a gate number) to gate the ECT data for image reconstruction. In some embodiments, the ECT data may be 4D data. As used herein, 4D data may refer to a data form containing time domain data and three dimensional (3D) spatial data. In some embodiments, the 4D data or a corresponding ECT image reconstructed based on the 4D data may be expressed as $\lambda(j,t)$, where j refers to a voxel (or an index) in the ECT image, the voxel corresponds to a spatial point of the subject, and t refers to a time axis (or a time point on the time axis). As used herein, "gate" may refer to that the ECT data may be divided into a plurality of sections along the time axis t and one of the sections may be selected to be processed to generate an ECT image. As used herein, "gate number" may refer to the number of the plurality of sections. In some embodiments, the coordinates of the time axis t may correspond to the gate number. For example, for a gate number n, the coordinates of the time axis t may be $\{1, 2, 3, \ldots, n\}$.

In some embodiments, during the acquisition of the ECT data, motions of the subject (e.g., respiratory motion or cardiac movements of the heart) may be unavoidable which may lead to motion blur in the ECT image reconstructed based on the ECT data. In order to reduce the motion blur, gating control unit 304 may gate the ECT data according to a gate number (e.g., n) into a plurality of sections and select one of the sections to reconstruct an ECT image. In some embodiments, the gate number may both influence the motion blur and the noise of the ECT image. For example, for a spatial point whose motion range is $A_0$ (it is supposed that $A_0 > \varepsilon$, where $\varepsilon$ is the intrinsic resolution of the imaging system), if the gate number is n, the motion blur of a voxel corresponding to the spatial point may be reduced to $A_0/n$, and the noise of the voxel may be increased by $\sqrt{n}$.

In some situations, for different spatial points of the subject, motion information (e.g., motion range) may be different. For example, the motion range by respiratory motion of a spatial point on the back of a subject may be approximately zero, while the motion range by respiratory motion of a spatial point of the chest of the subject may be relatively high. Relative to an ECT image reconstructed based on a non-gating approach, motion blur or noise of an ECT image reconstructed based on a gating approach may be modified. For example, for the ECT data acquired from the chest of the subject, to reduce the possible motion blur of voxels corresponding to the chest in the ECT image, a gate number of the gating approach may be determined based on the motion range of the chest. In the ECT image, the motion blur of the voxels corresponding to chest may be reduced, but the noise of the voxels corresponding the chest may be reduced. In this situation, if a same gate number is selected for the ECT data acquired from the back of the subject where the motion range is approximately zero, the noise of the voxels corresponding to the back may be reduced.

In some embodiments, considering that the motion ranges of different spatial points of a subject may be different, gating control unit 304 may determine different gate numbers for different ECT data acquired from different spatial points of the subject that correspond to different voxels in the ECT image. In some embodiments, gating control unit 304 may determine a motion curve indicative of the motion ranges of different spatial points of the subject and determine different gate numbers based on the motion curve. In some embodiments, while determining the plurality of gate numbers, gating control unit 304 may take both noise and motion blur into consideration. In some embodiments, gating control unit 304 may determine the gate numbers according to the motion ranges of the spatial points of the subject. In some embodiments, gating control unit 304 may determine the gate numbers according to an intermediate image against which value differences among voxels corresponding to the spatial points of the subject may be determined. Merely by way of example, a value of a voxel may refer to a grey level of the voxel. In some embodiments, gating control unit 304 may determine a temporal spread function based on the gate numbers, and further reconstruction unit 306 may reconstruct an ECT image based on the temporal spread function.

Reconstruction unit 306 may generate an ECT image relating to an object (e.g., a subject, or a portion thereof) based on the ECT data and the gate numbers. For example, reconstruction unit 306 may gate the ECT data based on the gate numbers and reconstruct the ECT image based on the gated ECT data. In some embodiments, reconstruction unit 306 may employ different kinds of image reconstruction techniques for the image reconstruction procedure. Exemplary image reconstruction techniques may include Fourier slice theorem, filtered back projection algorithm, fan-beam reconstruction, iterative reconstruction, or the like, or a combination thereof. In some embodiments, reconstruction unit 306 may include one or more sub-units (not shown). The sub-units may reconstruct images by employing different reconstruction techniques. In some embodiments, the reconstructed image may be stored in storage unit 308.

Storage unit 308 may store the ECT data processed by pre-processing unit 302, the ECT image reconstructed by reconstruction unit 306, and the gating parameters determined by gating control unit 304. In some embodiments, the storage format may include text, picture, audio, video, code, or the like, or a combination thereof. In some embodiments, one or more algorithms that may be used during the processing, the reconstruction, or the gating control process may be stored in storage unit 308. The algorithm may include a threshold segmentation algorithm, an iterative algorithm, an interpolation algorithm, a statistical algorithm, a smoothing filtering algorithm, or the like, or any combination thereof.

It should be noted that the above description of processing module 134 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the assembly and/or function of processing module 134 may be varied or changed. In some embodiments, one or more units in processing module 134 may include an independent storage block (not shown) respectively and storage unit 308 may be optional. In some embodiments, any two or more units may be integrated into an independent unit used to implement more than one functions. As another example, pre-processing unit 302 may be optional.

Figure 4:
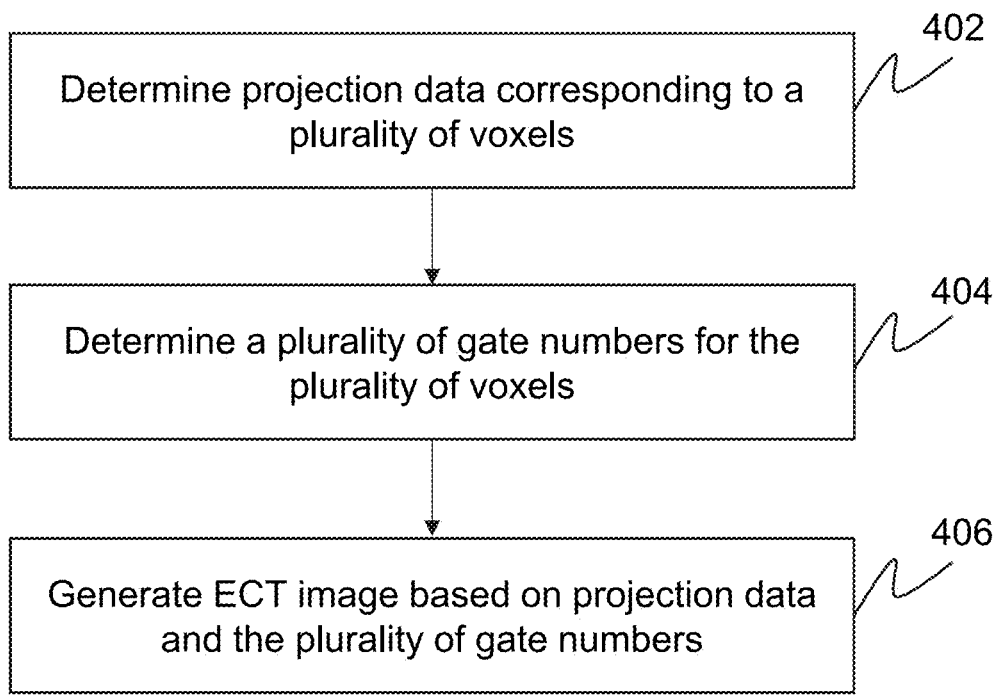
FIG. 4 is a flowchart illustrating an exemplary process for reconstructing an ECT image according to some embodiments of the present disclosure.

FIG. 4 is a flowchart illustrating an exemplary process for reconstructing an ECT image according to some embodiments of the present disclosure. In 402, processing module 134 may determine projection data corresponding to a plurality of voxels. The plurality of voxels may correspond to a plurality of spatial points of a subject. In some embodiments, the projection data may be 4D data. As used herein, 4D data may refer to a data form containing time domain data and three dimensional (3D) spatial data. In some embodiments, processing module 134 may determine the projection data based on the ECT data acquired by acquisition module 110.

In 404, gating control unit 304 may determine a plurality of gate numbers for the plurality of voxels, where at least two of the plurality of gate numbers may differ from each other. The plurality of gate numbers may be associated with motion information of the plurality of voxels. In some embodiments, gating control unit 304 may determine the gate numbers according to the motion ranges of the spatial points of the subject corresponding to the plurality of voxels (e.g., a motion curve). For example, the motion ranges of the spatial points may be determined or obtained from a data library or a population-based distribution approach. Under the data library or the population-based distribution approach, the respiratory motion and/or cardiac movement of the heart may be considered similar among human beings. The motion ranges of the spatial points of a subject may be determined based on statistical data or clinical data.

Further, under the data library or the population-based distribution approach, the information of respiratory motion may be classified according to a criterion (e.g., age, gender, height, weight, or the like, or a combination thereof). The cardiac movement information of the heart may be handled similarly. Under the data library or the population-based distribution approach, the information of the cardiac movement of the heart may be classified according to a criterion (e.g., age, gender, height, weight, or the like). The motion ranges of the spatial points of a subject may be determined with an improved accuracy.

Merely by way of example, gating control unit 304 may determine the plurality of gate numbers by equation (1) below, that is, each of the plurality of gate numbers is a ratio of the motion range of a spatial point corresponding to a voxel to the intrinsic resolution:

$$n(j)=A_0(j)/\varepsilon, \quad (1)$$

where j refers to the voxel index, $A_0(j)$ refers to the motion range of a spatial point corresponding to voxel j, $\varepsilon$ refers to the intrinsic resolution of the ECT system, and n(j) refers to the gate number for the voxel j.

In some embodiments, for different voxels, suitable gate numbers may be different under different situations. For example, if the ECT image is used for a noise-sensitive application, a suitable gate number for the voxel j may be less than $A_0(j)/\varepsilon$. If the image is used for a quantitative-sensitive application, a suitable gate number for voxel j may be greater than $A_0(j)/\varepsilon$.

In some embodiments, gating control unit 304 may determine the plurality of gate numbers based on an intermediate image. In some embodiments, the ECT data acquired from different spatial points corresponding to different voxels in the intermediate image may be gated according to a uniform gate number and the intermediate image may be generated based on the gated ECT data. As used herein, the intermediate image may be a 4D image. Based on the intermediate image, a difference between a voxel in the intermediate image at a first time point and a corresponding voxel at a second time point may be determined. As used herein, corresponding voxels may refer to voxels at different time points that correspond to a same spatial point of a subject in the intermediate image. In some embodiments, a difference image may be determined based on the difference. Gating control unit 304 may determine a plurality of gate numbers for the plurality of voxels based on the difference image. For example, the larger the value (e.g., a grey level) of a specific voxel in the difference image is, the greater the gate number may be for a corresponding voxel that corresponds to a same spatial point of a subject with the specific voxel.

In some embodiments, gating control unit 304 may further determine a feature relating to motion information of the plurality of voxels. For example, gating control unit 204 may determine a temporal spread function based on the plurality of gate numbers, and the feature relating to the motion information may be a Full Width at Half Maximum of the temporal spread function. In some embodiments, the temporal spread function may refer to a blurring effect (e.g., a Gaussian blur). In some embodiments, the temporal spread function may relate to spatial information and time information of the ECT data (or the projection data) acquired from different spatial points of a subject.

In 406, reconstruction unit 306 may generate an ECT image based on the projection data and the plurality of gate numbers. In some embodiments, gating control unit 304 or reconstruction unit 306 may gate the projection data based on the plurality of gate numbers. For example, for a specific voxel, gating control unit 304 or reconstruction unit 306 may gate the projection data acquired from a spatial point corresponding to the specific voxel along the time axis according to a corresponding gate number of the plurality of gate numbers; gated projection data may include the projection data for voxels and their respective gate numbers; reconstruction unit 306 may reconstruct an ECT image based on the gated projection data. In some embodiments, reconstruction unit 306 may reconstruct an ECT image based on the temporal spread function. In some embodiments, reconstruction unit 306 may generate the ECT image based on an image reconstruction algorithm. The image reconstruction algorithm may include Maximum Likelihood Expectation Maximization (MLEM) algorithm, Ordered Subset Expectation Maximization (OSEM) algorithm, Maximum Likelihood reconstruction of Attenuation and Activity (MLAA) algorithm, or the like, or a combination thereof.

Merely by way of example with reference to the reconstruction of a PET image, the distribution of the projection data of the voxels may be approximated by a Poisson distribution, and a likelihood function of the distribution of the projection data may be described by equation (2):

$$\mathcal{L}(x, p) = \prod_i (\hat{p}_i)^{p_i}(p_i!)^{-1}\exp(-\hat{p}_i), \qquad (2)$$

where $\mathcal{L}(x, p)$ refers to the likelihood function of the distribution of the projection data, x refers to the distribution of the projection data p$\rho$, i refers to the $i_{th}$ LOR of the projection data, and $\hat{p}_i$ refers to an estimation of the projection data of the $i^{th}$ LOR.

In some embodiments, the projection data may be estimated based on a projection matrix of the imaging system, an estimation of the distribution of the PET tracer within the subject, scattering events, or random events. As used herein, the projection matrix may be determined based on default settings of the imaging system, or provided by a user. The scattering events and random events may be determined based on statistical data or empirical data. For example, the estimation of the projection data may be determined by equation (3):

$$(\hat{p}=HF+S+R, \qquad (3)$$

where $\hat{p}$ refers to the estimation of the projection data, H refers to the projection matrix of the ECT system, F refers to a vector of an estimated PET image corresponding to an estimation of the distribution of the PET tracer within the subject (generally in a ECT process, F refers to an estimated ECT image), S refers to scattering events, and R refers to the random events.

In some embodiments, the estimated ECT image may be determined based on a first substituted ECT image by a first interpolation function. As used herein, the first substituted ECT image may refer to an ECT image corresponding to the distribution of the ECT tracer within the subject. For different voxels (or different spatial points of the subject) in the first substituted ECT image, the coordinates of the time axis may be different; that is, for different voxels, the lengths of the time axis may be different. For example, for voxel j, the coordinates of the time axis may be {1, 2, 3,. . . , n(j)}, and the length of the time axis may be n(j), where n(j) is an integer.

For example, the estimated ECT image may be determined based on the first substituted ECT image by equation (4):

$$F(j, g) = \sum_{t=1}^{n(j)} u_j(g, t)\lambda(j, t), \qquad (4)$$

where j refers to the voxel index, g and t refer to temporal indexes (also referred to as the "coordinates of the time axis"), F(j,g) refers to the estimated ECT image, $\lambda$(j,t) refers to the first substituted ECT image, and $u_j$(g,t) refers to the first interpolation function.

In some embodiments, in the estimated ECT image determined based on the first substituted ECT image, for different voxels (or different spatial points of the subject), the coordinates of the time axis is uniform; that is, for different voxels, the lengths of the time axis is uniform (i.e., G, the maximum one of the plurality of gate numbers (also referred to as a "threshold"relating to the plurality of gate numbers)). For example, for voxel j, the length of the time axis is G, and the gate number may be n(j), where n(j) may be an integer or not. Under actual operation, an integer is suitable for the value of n(j), while under theoretical case, a non-integer is suitable for the value of n(j).

In some embodiments, the first interpolation function may include a linear interpolation function, a cubic interpolation function, a spline interpolation function, or the like, or a combination thereof. For example, the first interpolation function may be expressed as equation (5):

$$u_j(g, t) = \begin{cases} 0, t \neq \left\lfloor \frac{g*n(j)}{G} \right\rfloor, & t \neq \left\lfloor \frac{g*n(j)}{G} \right\rfloor + 1 \\ \left\{ \frac{g*n(j)}{G} \right\}, & t = \left\lfloor \frac{g*n(j)}{G} \right\rfloor + 1, \\ 1 - \left\{ \frac{g*n(j)}{G} \right\}, & t = \left\lfloor \frac{g*n(j)}{G} \right\rfloor \end{cases} \qquad (5)$$

where j refers to the voxel index, g and t refer to temporal indexes, n(j) refers to the gate number determined for the $j^{th}$ voxel (also referred to as the "length of the time axis"), G refers to the maximum gate number of the plurality of gate numbers, symbol [x] refers to a function for determining a maximum integer which is less than or equal to x, and symbol {x} refers to a function for determining a fractional part of x, that is, {x}=–[x].

In some embodiments, the first substituted ECT image may be determined based on a second substituted ECT image by a second interpolation function. For different voxels in the second substituted ECT image, the coordinates of the time axis may be uniform; that is, for different voxels, the lengths of the time axis may be uniform (G, the maximum one of the plurality of gate numbers). For voxel j, the length of the time axis is G, and the gate number may be n(j), where n(j) is an integer or not. For example, the first substituted ECT image may be determined by equation (6):

$$\lambda(j, t) = \sum_{\tau=1}^{G} (v_j(t, \tau)f(j, \tau)), \qquad (6)$$

where j refers to the voxel index, $\tau$and t refer to temporal indexes, G refers to the uniform length of the time axis (i.e., the maximum one of the plurality of gate numbers), $\lambda$(j,t) refers to the first substituted ECT image, $v_j$(t,$\tau$) refers to the second interpolation function, and f(I,T) refers to the second substituted ECT image.

In some embodiments, considering that the first substituted ECT image may be determined by the second substituted ECT image, there may be a relationship between the estimated ECT image and the second substituted ECT image. For example, the estimated ECT image and the second substituted ECT image may be linked by a temporal spread function as expressed in equation (7):

$$F(j, g) = \sum_{\tau=1}^{G} w_j(g, \tau)f(j, \tau), \qquad (7)$$

where j refers to the voxel index, g and τ refer to temporal indexes, G refers to the uniform length of the time axis (i.e., the maximum gate number of the plurality of gate numbers), F(j,g) refers to the estimated ECT image, f (j, τ) refers to the second substituted ECT image, and $w_j(g, \tau)$ refers to the temporal spread function.

In some embodiments, the temporal spread function may be determined by the first interpolation function. For example, the estimated ECT image may be determined by equation (8):

$$F(j, g) = \sum_{t=1}^{n(j)} u_j(g, t)\lambda(j, t) = \sum_{t=1}^{n(j)} u_j(g, t) \sum_{\tau=1}^{G} (v_j(t, \tau) f(j, \tau)) = \sum_{\tau=1}^{G} w_j(g, \tau) f(j, \tau), \quad (8)$$

where j refers to the voxel index, g, and t refer to temporal indexes, G refers to the uniform length of the time axis (i.e., the maximum gate number of the plurality of gate numbers), F(j,g) refers to the estimated ECT image, λ(j,t) refers to the first substituted ECT image, $u_j(g,t)$ and $v_j(t, \tau)$ refer to the first interpolation function and the second interpolation function, respectively, f (j, τ) refers to the second substituted ECT image, and $w_j(g, \tau)$ refers to the temporal spread function.

Therefore, the temporal spread function may be determined by equation (9):

$$w_j(g, \tau) = \sum_{t=1}^{n(j)} u_j(g, t) v_j(t, \tau), \quad (9)$$

where j refers to the voxel index, g and t refer to temporal indexes, $u_j(g,t)$ and $v_j(t, \tau)$ refer to the first interpolating function and the second interpolating function, respectively, n(j) refers to the gate number determined for the $j^{th}$ voxel, and $w_j(g, \tau)$ refers to the temporal spread function. For voxel j, the gate number n(j) may not be an integer.

In some embodiments, the temporal spread function may be determined based on the plurality of gate numbers. In some embodiments, the temporal spread function may be determined by a blurring function (e.g., a Gaussian blurring function). In some embodiments, the Full Width at Half Maximum (FWHM) of the blurring function may equal to G/n(j). For example, the time spread function may be determined by equation (10):

$$w_j(g, \tau) = \frac{1}{C_g} \exp\left(-\ln(2) \frac{4(\tau - g)^2}{(G/n(j))^2}\right), \quad (10)$$

where j refers to the voxel index, g and τ refer to temporal indexes, G refers to the uniform length of the time axis (i.e., the maximum gate number of the plurality of gate numbers), n(j) refers to the gate number for the $j^{th}$ voxel, and $C_g$ refers to a constant value. $C_g$ may be determined by $\Sigma_\tau w_j(g,\ )=1$. As another example, the temporal spread function may be determined by equation (11):

$$w_j(g, \tau) = \begin{cases} 1, & \tau = g \\ 0, & \text{Otherwise} \end{cases}, \quad (11)$$

where j refers to the voxel index, and g and τ refer to temporal indexes.

In some embodiments, the first substituted ECT image may be determined by combining equation (3) and equation (4) with the MLEM algorithm. An iterative function for the first substituted ECT image may be determined by equation (12):

$$\lambda_{j,t}^{m+1} = \frac{\lambda_{j,t}^m}{\sum_g u_{j,g,t} \sum_i H_{i,j}} \sum_g u_{j,g,t} \sum_i \frac{H_{i,j} P_{i,g}}{\sum_k H_{i,k} \sum_\tau u_{k,g,t} \lambda_{k,t}^m + S_g + R_g}, \quad (12)$$

where j and k refer to voxel indexes, g, τ, and t refer to temporal indexes, m refers to the iterative index, u refers to the first interpolating function, H refers to the projection matrix of the ECT system, S refers to the scattering events, R refers to the random events, P refers to the projection data, and τ refers to the first substituted ECT image.

In some embodiments, the second substituted ECT image may be determined by combining equation (4) and equation (7) with the MLEM algorithm. An iterative function for the second substituted ECT image may be determined by equation (13):

$$f_{j,\tau}^{m+1} = \frac{f_{j,\tau}^m}{\sum_g w_{j,g,\tau} \sum_i H_{i,j}} \sum_g w_{j,g,\tau} \sum_i \frac{H_{i,j} P_{i,g}}{\sum_k H_{i,k} \sum_\tau w_{k,g,\tau} \lambda_{k,\tau}^m + S_g + R_g}, \quad (13)$$

where j and k refer to voxel indexes, g, τ, and t refer to temporal indexes, m refers to the iterative index, w refers to the temporal spread function, H refers to the projection matrix of the ECT system, S refers to the scattering events, R refers to the random events, P refers to the projection data, and f refers to the second substituted ECT image.

In some embodiments, the iterative function may begin with a uniform distribution estimation. To identify a difference between the estimated projection data and the actually measured projection data, they may be compared during the iteration process. During the iterative process, the estimated projection data may be updated and a new iteration may be performed. The difference between the estimated projection data and the actually measured projection data may be reduced during the iterative process. In some embodiments, the iterative process may proceed until the difference between the estimated projection data and the actually measured projection data is less than a threshold value. In some embodiments, the iterative process may proceed until the difference between the estimated projection data and the actually measured projection data stables—the change of the differences between a certain number (e.g., 2, 3, 4) of consecutive iterations falls within a threshold value. In some embodiments, the iterative process may proceed until the number of iterations that have been performed exceeds a threshold value. The threshold value may be determined based on default settings of imaging system, or provided by a user.

In some embodiments, the estimated ECT image may be determined based on the first substituted ECT image or the second substituted ECT image. In some embodiments, image processing system 100 may generate an ECT image based on the estimated ECT image, the first substituted ECT image, and/or the second substitute ECT image.

Figure 5:
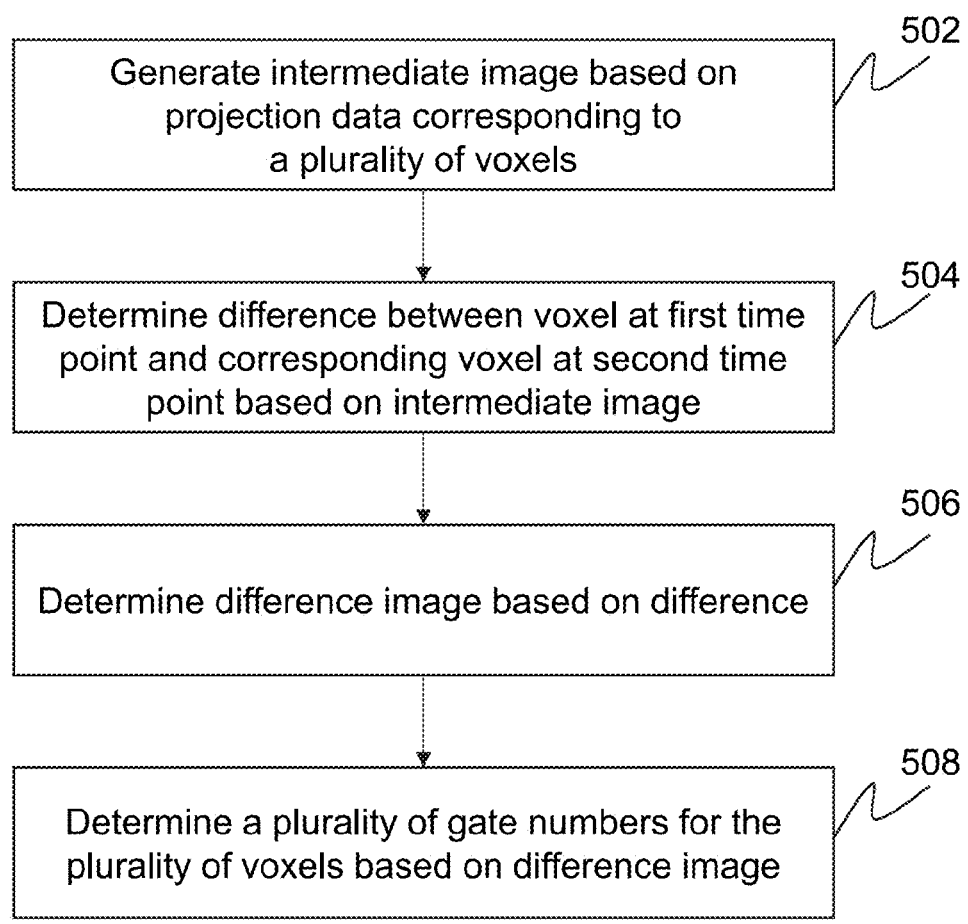
FIG. 5 is a flowchart illustrating an exemplary process for determining gate numbers for reconstructing an ECT image according to some embodiments of the present disclosure.

FIG. 5 is a flowchart illustrating an exemplary process for determining a plurality of gate numbers for a plurality of voxels according to some embodiments of the present disclosure. In 502, gating control unit 304 may generate an intermediate image based on the projection data corresponding to a plurality of voxels. For example, gating control unit 304 may gate the projection data according to a uniform gate number for the plurality of voxels.

In 504, gating control unit 304 may determine a difference between a voxel at a first time point and a corresponding voxel at a second time point based on the intermediate image. As used herein, corresponding voxels may refer to voxels at different time points that correspond to a same spatial point of a subject in the intermediate image. For example, the difference may be determined by x (j, g)–x (j, t), where j refers to the voxel index, g and t refer to temporal indexes, x (j,t) refers to the value (e.g., a grey level) of the $j^{th}$ voxel at time point t, and x (j,g) refers to the value (e.g., a grey level) the $j^{th}$ voxel at time point g.

In 506, gating control unit 304 may determine a difference image based on the difference determined in 504. For example, the difference image may be determined by equation (14):

$$D(j, t) = \sqrt{\sum_{g=1}^{G} (x(j, g) = x(j, t))^2} \bigg/ \sum_{g=1, g \neq t}^{G} x(j, g), \quad (14)$$

where j refers to the voxel index, g and t refer to temporal indexes, G refers to the uniform length of the time axis (i.e., the maximum one of the plurality of gate numbers), x (j,t) refers to the value of the $j^{th}$ voxel at time point t, x (j, g) refers to the value of the $j^{th}$ voxel at time point g, and D(j,t) refers to the difference image.

In 508, gating control unit 304 may determine a plurality of gate numbers for the plurality of voxels based on the difference image. For example, for the $j^{th}$ voxel, the larger the value of the voxel at time point t in the difference image is, the greater the gate number may be for the $j^{th}$ voxel. For example, the gate number for the $j^{th}$ voxel may be determined by equation (13):

$$n(j) = G * \frac{\max_t(D(j, t))}{\max_{t,j}(D(j, t))}, \quad (15)$$

where n(j) refers to the gate number for the $j^{th}$ voxel, G refers to the uniform length of the time axis (i.e., the maximum gate number of the plurality of gate numbers), and D(j,t) refers to the value of the $j^{th}$ voxel at time point t in the difference image.

After the plurality of gate numbers are determined, gating control unit 304 may further determine the temporal spread function according to equation (10).

Figure 6:
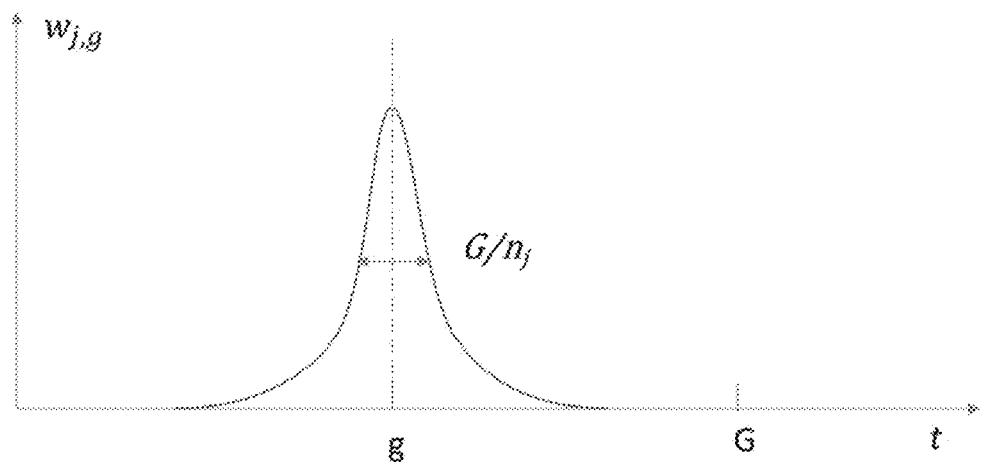
FIG. 6 is a schematic diagram illustrating an exemplary temporal spread function according to some embodiments of the present disclosure.

In some embodiments, the temporal spread function illustrated in FIG. 6 may be determined based on the difference image. For example, the larger the value of the $j^{th}$ voxel at time point t in the difference image is, the lower the value of the FWHM of the temporal spread function may be.

FIG. 6 is a schematic diagram illustrating an exemplary temporal spread function according to some embodiments of the present disclosure. As illustrate in FIG. 6, the curve may donate an exemplary temporal spread function for the $j^{th}$ voxel varying with time t. The FWHM of the curve equals to G/n(j). The greater the value of the FWHM is, the smoother the curve of the temporal function may be. In some embodiments, the value of the FWHM may be determined based on the motion range of the spatial point of the subject corresponding to a voxel. For example, the value of the FHWM may be determined based on the difference image described with reference to FIG. 5. In some embodiments, the FWHM may be determined by G/n(j), where G refers to the uniform length of the time axis (i.e., the maximum gate number of the plurality of gate numbers), and n(j) refers to the gate number for the $j^{th}$ voxel.

EXAMPLES

The following examples are provided for illustration purposes, and not intended to limit the scope of the present disclosure.

Example 1

FIG. 7-A, FIG. 7-B, and FIG. 7-C illustrate exemplary ECT images regarding a portion of a patient generated by different reconstruction approaches according to some embodiments of the present disclosure. For illustration purposes, 2D images are shown. The ECT image illustrated in FIG. 7-A was reconstructed based on the projection data that was processed based on the temporal spread function described in this disclosure. The ECT image illustrated in FIG. 7-B was reconstructed based on a non-gating approach (e.g., a point spread function approach). The ECT image illustrated in FIG. 7-C was reconstructed based on the projection data that was gated according to a uniform gate number.

It may be seen that the ECT image in FIG. 7-B has a low noise level but poor image resolution. The ECT image in FIG. 7-C has a high image resolution but high noise level. The ECT image in FIG. 7-A has a high noise level and a high image resolution. The noise level of the ECT image illustrated in FIG. 7-A is similar to that in FIG. 7-B. The image resolution of the ECT image illustrated in FIG. 7-A is similar to that in FIG. 7-C. Example 2

FIG. 8-A, FIG. 8-B, and FIG. 8-C illustrate exemplary ECT images regarding phantom generated by different reconstruction approaches according to some embodiments of the present disclosure. For illustration purposes, 2D images are shown. The ECT image illustrated in FIG. 8-A was reconstructed based on the projection data that was processed based on the temporal spread function described in this disclosure. The ECT image illustrated in FIG. 8-B was reconstructed based on a non-gating approach (e.g., a point spread function method). The ECT image illustrated in FIG. 8-C was reconstructed based on the projection data that was gated according to a uniform gate number. It may be seen that the ECT image in FIG. 8-B has a low noise level but poor image resolution. The ECT image in FIG. 8-C has a high image resolution but high noise level. The ECT image in FIG. 8-A has a low noise level and a high image resolution. The noise level of the ECT image illustrated in FIG. 8-A is similar to that in FIG. 8-B. The image resolution of the ECT image illustrated in FIG. 8-A is similar to that in FIG. 8-C.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method for reconstructing an Emission Computed Tomography (ECT) image implemented on at least one machine each of which has at least one processor and storage, the method comprising:
    obtaining ECT projection data, the ECT projection data corresponding to a plurality of voxels in reconstructed image domain;
    determining a plurality of gate numbers for the plurality of voxels, the plurality of gate numbers relating to motion information of the plurality of voxels;
    determining a feature relating to the motion information of the plurality of voxels based on the plurality of gate numbers; and
    reconstructing an ECT image based on the ECT projection data and the feature.

2. The method of claim 1, wherein the ECT projection data includes four-dimensional (4D) Single Photon emission Computed Tomography (SPECT) data, 4D Positron Emission Tomography (PET) data, or 4D Computed Tomography (CT) data.

3. The method of claim 1, wherein each of the gate numbers is corresponding to one or more of the plurality of voxels.

4. The method of claim 1, wherein each of the plurality of gate numbers is equal to a ratio of a motion range of the voxel to intrinsic resolution of an ECT scanner which is adapted for scanning a subject.

5. The method of claim 1, wherein the determining the plurality of gate numbers for the plurality of voxels includes:
    obtaining, from a population-based distribution, a plurality of motion ranges of the plurality of voxels; and
    determining the plurality of gate numbers based on the plurality of motion ranges.

6. The method of claim 1, wherein the determining the plurality of gate numbers for the plurality of voxels includes:
    generating an intermediate image based on the ECT projection data;
    determining a difference between the plurality of voxels at a first time point and the plurality of voxels at a second time point based on the intermediate image;
    determining a difference image based on the difference; and
    determining the plurality of gate numbers based on the difference image.

7. The method of claim 1, further comprising:
    determining a temporal spread function based on the plurality of gate numbers; and
    obtaining the feature relating to the motion information of the plurality of voxels based on the temporal spread function.

8. The method in claim 7, wherein the temporal spread function is a blurring function.

9. The method of claim 7, wherein the feature includes a Full Width at Half Maximum of the temporal spread function.

10. The method of claim 7, wherein the determining the feature relating to the motion information includes:
    determining a threshold relating to the plurality of gate numbers; and
    determining the Full Width at Half Maximum of the temporal spread function based on the plurality of gate numbers and the threshold.

11. The method of claim 10, wherein the threshold relating to the plurality of gate numbers is the maximum one of the plurality of gate numbers.

12. The method of claim 1, wherein the determining the plurality of gate numbers for the plurality of voxels includes:
    determining a first gate number for a first voxel of the plurality of voxels; and
    determining a second gate number for a second voxel of the plurality of voxels, the second gate number differing from the first gate number.

13. The method of claim 12, further including:
    determining a first Full Width at Half Maximum of a first temporal spread function for the first voxel, the first Full Width at Half Maximum corresponding to a first motion range of the first voxel; and
    determining a second Full Width at Half Maximum of a second temporal spread function for the second voxel, the second Full Width at Half Maximum corresponding to a second motion range of the second voxel, the second Full Width at Half Maximum differing from the first Full Width at Half Maximum.

14. A method for reconstructing an Emission Computed Tomography (ECT) image, implemented on at least one machine each of which has at least one processor and storage, the method comprising:
    obtaining ECT projection data of a subject;
    generating an intermediate image based on the ECT projection data, wherein the intermediate image comprises a plurality of voxels;
    determining a plurality of gate numbers for the plurality of voxels in the intermediate image, the plurality of gate numbers relating to motion information of the plurality of voxels;
    determining a feature based on the plurality of gate numbers; and
    reconstructing an ECT image of the subject based on the ECT projection data and the feature.

15. The method of claim 14, wherein determining the plurality of gate numbers for the plurality of voxels in the intermediate image includes:
    determining a difference between the plurality of voxels at a first time point and the plurality of voxels at a second time point in the intermediate image;
    determining a difference image using the difference; and
    determining the plurality of gate numbers based on the difference image.

16. The method of claim 14, wherein the reconstructing an ECT image of the subject based on the ECT projection data and the feature includes:
    sorting the ECT projection data of the subject into a plurality of bins according to the plurality of gate numbers; and reconstructing the ECT image based on at least one of the plurality of bins.

17. The method of claim 14, wherein the ECT projection data comprises at least one of 4D SPECT data, 4D PET data, or 4D CT data.

18. The method of claim 14, wherein the determining a feature based on the plurality of gate numbers includes:
   determining a temporal spread function based on the plurality of gate numbers;
   determining the feature based on the temporal spread function, wherein the feature relates to the motion information of the plurality of voxels.

19. An Emission Computed Tomography (ECT) system comprising:
   a set of instructions for ECT image reconstruction, and
   one or more processors, when executing the set of instructions, the one or more processors are directed to:
      obtain ECT projection data, the ECT projection data corresponding to a plurality of voxels;
      determine a plurality of gate numbers for the plurality of voxels, the plurality of gate numbers relating to motion information of the plurality of voxels;
      determine a feature relating to the motion information of the plurality of voxels based on the plurality of gate numbers; and
      reconstruct an ECT image based on the ECT projection data and the feature.

* * * * *